United States Patent
Song et al.

(10) Patent No.: US 10,350,539 B2
(45) Date of Patent: *Jul. 16, 2019

(54) METHOD OF RECOVERING (METH)ACRYLIC ACID

(71) Applicant: LG CHEM, LTD., Seoul (KR)

(72) Inventors: Jong Hun Song, Daejeon (KR); Se Won Baek, Daejeon (KR); Yoon Jae Min, Daejeon (KR); Jae Yul Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/082,424

(22) PCT Filed: Dec. 5, 2017

(86) PCT No.: PCT/KR2017/014152
§ 371 (c)(1),
(2) Date: Sep. 5, 2018

(87) PCT Pub. No.: WO2018/105993
PCT Pub. Date: Jun. 14, 2018

(65) Prior Publication Data
US 2019/0083923 A1    Mar. 21, 2019

(30) Foreign Application Priority Data

Dec. 6, 2016  (KR) .................. 10-2016-0165309
Dec. 4, 2017  (KR) .................. 10-2017-0164979

(51) Int. Cl.
| | | |
|---|---|---|
| *C07C 51/43* | (2006.01) | |
| *B01D 53/14* | (2006.01) | |
| *C07C 51/46* | (2006.01) | |
| *C07C 51/48* | (2006.01) | |
| *B01D 11/04* | (2006.01) | |
| *B01D 3/36* | (2006.01) | |
| *C07C 57/04* | (2006.01) | |

(52) U.S. Cl.
CPC ......... *B01D 53/1487* (2013.01); *B01D 3/36* (2013.01); *B01D 11/0488* (2013.01); *B01D 11/0492* (2013.01); *B01D 53/1418* (2013.01); *B01D 53/1425* (2013.01); *B01D 53/1456* (2013.01); *B01D 53/1493* (2013.01); *C07C 51/43* (2013.01); *C07C 51/46* (2013.01); *C07C 51/48* (2013.01); *C07C 57/04* (2013.01); *B01D 11/043* (2013.01); *B01D 11/0434* (2013.01); *B01D 11/0438* (2013.01); *B01D 2252/103* (2013.01); *B01D 2257/80* (2013.01)

(58) Field of Classification Search
CPC ......... C07C 57/04; C07C 51/43; C07C 51/46; C07C 51/48; B01D 11/043; B01D 11/0434; B01D 11/0438; B01D 11/0488; B01D 11/0492; B01D 2252/103; B01D 2257/80; B01D 3/36; B01D 53/1418; B01D 53/1425; B01D 53/1456; B01D 53/1487; B01D 53/1493
See application file for complete search history.

(56) References Cited

U.S. PATENT DOCUMENTS

| | | |
|---|---|---|
| 7,071,348 B2 | 7/2006 | Godbole et al. |
| 7,368,602 B2 | 5/2008 | Sakai et al. |
| 7,566,804 B2 | 7/2009 | Diefenbacher et al. |
| 8,246,790 B2 | 8/2012 | Baek et al. |
| 9,517,997 B2 | 12/2016 | Baek et al. |
| 9,718,756 B2 | 8/2017 | Baek et al. |
| 9,902,679 B2 | 2/2018 | Yoo et al. |
| 2010/0022478 A1 | 9/2010 | Baek et al. |
| 2015/0203431 A1* | 7/2015 | Baek ............... C07C 51/46 562/600 |

FOREIGN PATENT DOCUMENTS

| | | |
|---|---|---|
| EP | 3404015 A1 | 11/2018 |
| JP | 2009263347 A | 11/2009 |
| JP | 2009263351 A | 11/2009 |
| KR | 10-0349602 B1 | 8/2002 |
| KR | 10-2009-0041355 A | 4/2009 |
| KR | 10-2009-0108099 A | 10/2009 |
| KR | 10-0999428 A | 12/2010 |
| KR | 10-2015-0032046 A | 3/2015 |
| KR | 10-1546464 A | 8/2015 |
| KR | 10-2016-0032994 A | 3/2016 |
| KR | 10-2016-0057928 A | 5/2016 |
| KR | 10-1659541 B1 | 9/2016 |

* cited by examiner

*Primary Examiner* — Jafar F Parsa
*Assistant Examiner* — Blaine G Doletski
(74) *Attorney, Agent, or Firm* — Dentons US LLP

(57) ABSTRACT

The present invention relates to a method of recovering (meth)acrylic acid and an apparatus used for the recovery method. The recovery method according to the present invention discharges each (meth)acrylic acid aqueous solution of different concentrations at a (meth)acrylic acid absorption tower, and uses an extraction solvent of a specific ratio in the step of extracting (meth)acrylic acid, thus enabling the operation of a continuous process of recovering (meth)acrylic acid that can secure a high (meth)acrylic acid recovery rate, and can simultaneously significantly reduce purification energy cost.

9 Claims, 2 Drawing Sheets

METHOD OF RECOVERING (METH)ACRYLIC ACID

CROSS-REFERENCE(S)

Figure 1:
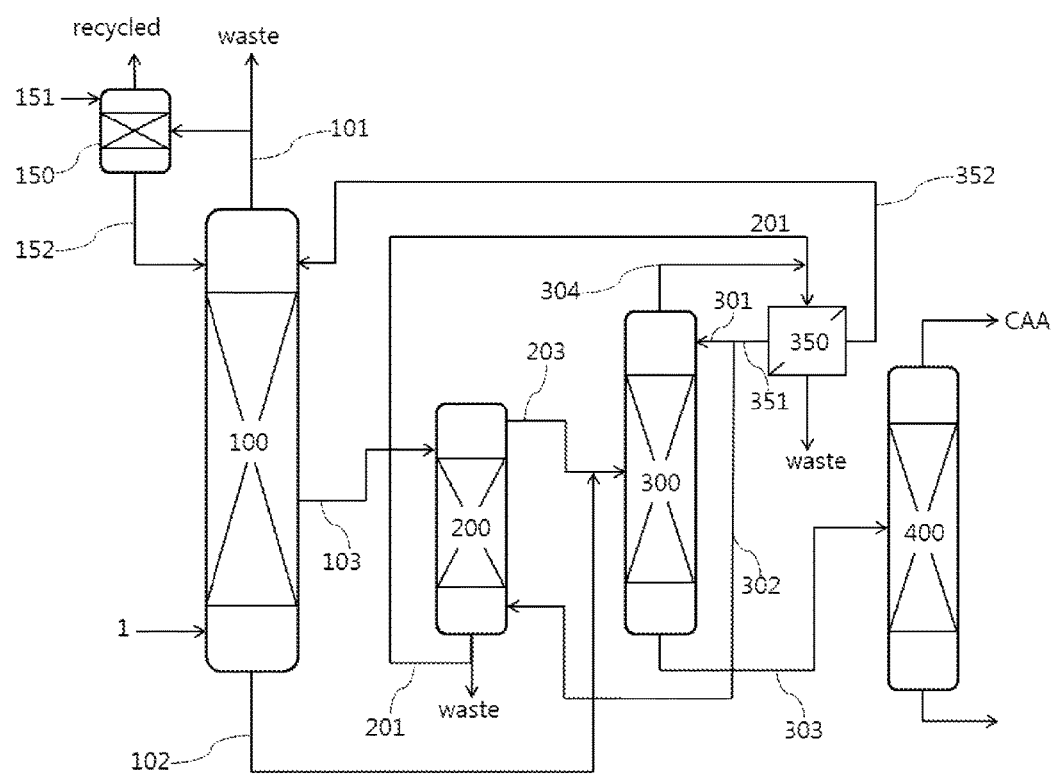

This application is a National Stage Entry of International Application No. PCT/KR2017/014152, filed on Dec. 5, 2017, and claims the benefit of and priority to Korean Application No. 10-2016-0165309, filed on Dec. 6, 2016, and Korean Application No. 10-2017-0164979, filed on Dec. 4, 2017, all of which are hereby incorporated by reference in their entirety for all purposes as if fully set forth herein.

TECHNICAL FIELD

The present invention relates to a method for recovering (meth)acrylic acid.

BACKGROUND OF THE ARTS (Meth)acrylic acid is generally prepared by gas phase oxidation of propane, propylene, (meth)acrolein, and the like in the presence of a catalyst. For example, propane, propylene, and the like are converted to (meth)acrylic acid through (meth)acrolein by gas phase oxidation in the presence of an appropriate catalyst in a reactor, and a mixed gas (1) including (meth)acrylic acid, non-reacted propane or propylene, (meth)acrolein, an inert gas, carbon dioxide, water vapor, and various organic byproducts (acetic acid, heavies, and the like) is obtained in the back end of the reactor.

The (meth)acrylic acid-containing mixed gas (1) contacts an absorption solvent such as process water in a (meth)acrylic acid absorption tower (100), and is recovered as a (meth)acrylic acid aqueous solution. Further, a (meth)acrylic acid-stripped insoluble gas is recycled for a synthesis reaction of (meth)acrylic acid, and a part thereof is incinerated and discharged. The (meth)acrylic acid aqueous solution is distilled and purified to obtain (meth)acrylic acid.

Meanwhile, various methods of controlling process conditions or process sequences and the like to improve the recovery efficiency of (meth)acrylic acid have been suggested. Representatively, as a method for separating water and acetic acid from the (meth)acrylic acid aqueous solution obtained in the (meth)acrylic acid absorption tower (100), an azeotropic distillation method using a hydrophobic solvent in a distillation column is known. As another method, a (meth)acrylic acid aqueous solution is fed to a (meth)acrylic acid extraction tower (200), and using a hydrophobic solvent, a (meth)acrylic acid extract solution with reduced water content and a raffinate solution thereof are obtained, and the extract is distilled, thereby reducing energy consumption.

However, in the known method of recovering (meth)acrylic acid, the (meth)acrylic acid absorption tower (100) discharges the aqueous solution of a single stream to the lower part, and there are limitations in that if the concentration of discharged (meth)acrylic acid aqueous solution is to be increased, the separation efficiency of the (meth)acrylic acid absorption tower (100) may be lowered, and if the concentration of discharged (meth)acrylic acid aqueous solution is maintained low so as to increase separation efficiency, purification (or distillation) load in the subsequent purification (or distillation) process may increase.

DETAILED DESCRIPTION OF THE INVENTION

Technical Problems

It is an object of the present invention to provide a method of recovering (meth)acrylic acid that can secure a high (meth)acrylic acid recovery rate, and simultaneously, that can further reduce purification energy costs.

Technical Solutions

The present invention provides a method of recovering (meth)acrylic acid including the steps of:

A) contacting a mixed gas including (meth)acrylic acid, organic byproducts, and water vapor with water in a (meth)acrylic acid absorption tower to form an aqueous solution of (meth)acrylic acid;

B) discharging the (meth)acrylic acid aqueous solution of a first concentration in a side part of the (meth)acrylic acid absorption tower;

C) discharging the (meth)acrylic acid aqueous solution of a second concentration in a lowest part of the (meth)acrylic acid absorption tower;

B-1) contacting the (meth)acrylic acid aqueous solution of the first concentration discharged to the side part with an extraction solvent including a hydrophobic organic solvent in the (meth)acrylic acid extraction tower, to extract (meth)acrylic acid; and D) distilling the (meth)acrylic acid extract obtained in step B-1) and the (meth)acrylic acid aqueous solution of the second concentration discharged in step C), through an azeotropic distillation process, to obtain (meth)acrylic acid, wherein the first concentration has a lower (meth)acrylic acid concentration than the second concentration, and the following Mathematical Formula 1 is satisfied:

$$Y1 = a \times X1 \quad \text{[Mathematical Formula 1]}$$

wherein, in Mathematical Formula 1,

Y1 is an amount of the extraction solvent used in step B-1), a is a ratio of the extraction solvent, and is equal to or greater than 2.5, and X1 is an amount of water included in the (meth)acrylic acid aqueous solution of the first concentration.

Advantageous Effects

The recovery method according to the present invention discharges each (meth)acrylic acid aqueous solution of different concentrations to a (meth)acrylic acid absorption tower, and thereafter, extracts and distills (meth)acrylic acid through separate processes, thus enabling the operation of the continuous process of recovering (meth)acrylic acid that can secure a high (meth)acrylic acid recovery rate, and simultaneously, can significantly reduce purification energy costs.

BRIEF DESCRIPTIONS OF DRAWINGS

Figure 2:
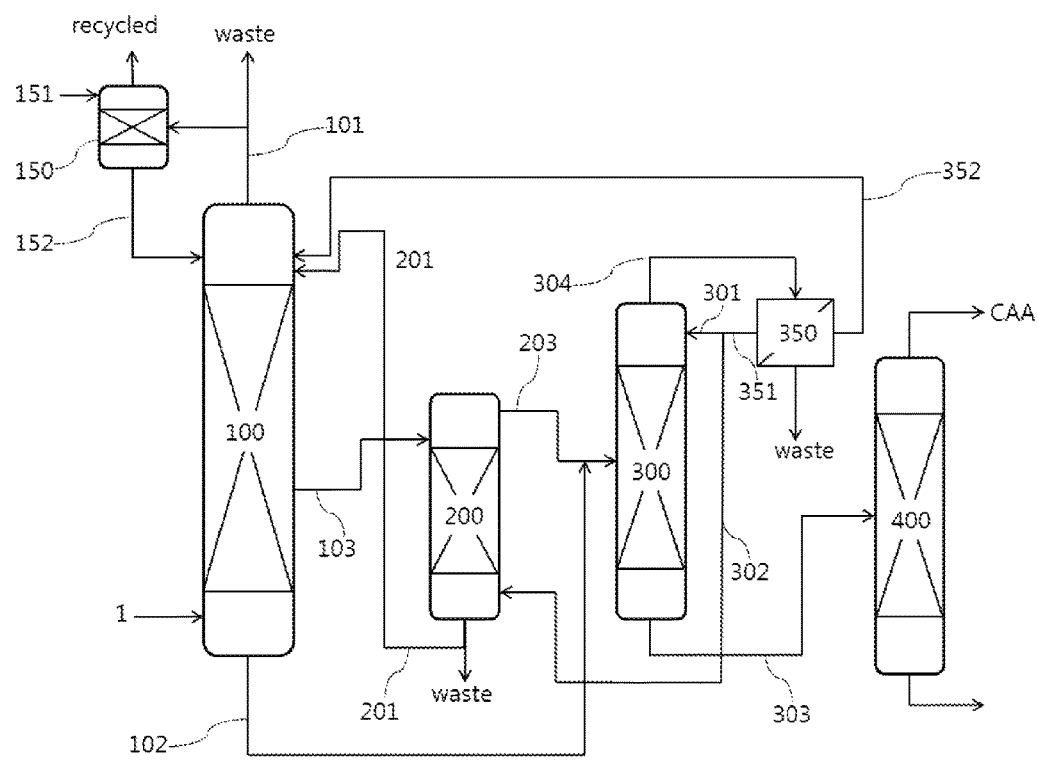

FIGS. 1 and 2 are process drawings of the method of recovering (meth)acrylic acid according to the embodiments of the present invention.

DETAILED EMBODIMENTS OF THE INVENTION

The method of recovering (meth)acrylic acid includes the steps of:

A) contacting a mixed gas including (meth)acrylic acid, organic byproducts, and water vapor with water in a (meth)acrylic acid absorption tower to form an aqueous solution of (meth)acrylic acid;

B) discharging the (meth)acrylic acid aqueous solution of a first concentration, in a side part of the (meth)acrylic acid absorption tower;

C) discharging the (meth)acrylic acid aqueous solution of a second concentration, in a lowest part of the (meth)acrylic acid absorption tower;

B-1) contacting the (meth)acrylic acid aqueous solution of the first concentration discharged to the side part with an extraction solvent including a hydrophobic organic solvent in the (meth)acrylic acid extraction tower, to extract (meth) acrylic acid; and D) distilling the (meth)acrylic acid extract obtained in step B-1) and the (meth)acrylic acid aqueous solution of the second concentration discharged in step C), through an azeotropic distillation process, to obtain (meth)acrylic acid, wherein the first concentration has a lower (meth)acrylic acid concentration than the second concentration, and the following Mathematical Formula 1 is satisfied:

$$Y1 = a \times X1 \qquad \text{[Mathematical Formula 1]}$$

wherein, in Mathematical Formula 1,

Y1 is an amount of the extraction solvent used in step B-1), a is a ratio of the extraction solvent, and is equal to or greater than 2.5, and X1 is an amount of water included in the (meth)acrylic acid aqueous solution of the first concentration.

As used herein, terms "first", "second" and the like are used to explain various constructional elements, and they are used only to distinguish one constructional element from other constructional elements.

The terms used herein are only to explain specific embodiments, and are not intended to limit the present invention. A singular expression includes a plural expression thereof, unless it is expressly stated or obvious from the context that such is not intended. As used herein, the terms "comprise", "have", etc. are intended to designate the existence of practiced characteristics, numbers, steps, constructional elements, or combinations thereof, and they are not intended to preclude the possibility of existence or addition of one or more other characteristics, numbers, steps, constructional elements, or combinations thereof.

In case it is stated that each constructional element is formed "on" or "above" each construction element, it means that each constructional element is formed directly on each constructional element, or that other constructional elements may be additionally formed between the layers or on the object or substrate.

Although various modifications can be made to the present invention and the present invention may have various forms, specific examples will be illustrated and explained in detail below. However, it should be understood that these are not intended to limit the present invention to a specific disclosure, and that the present invention includes all modifications, equivalents, or replacements thereof without departing from the spirit and technical scope of the invention.

Throughout the specification, the term '(meth)acrylic acid' generally refers to acrylic acid, methacrylic acid, or a mixture thereof.

The term 'mixed gas including (meth)acrylic acid' generally refers to a mixed gas that may be produced when (meth)acrylic acid is prepared by gas phase oxidation. That is, according to one embodiment of the present invention, the mixed gas including (meth)acrylic acid may be obtained by gas phase oxidation of at least one compound selected from the group consisting of propane, propylene, butane, i-butylene, t-butylene, and (meth)acrolein ('raw material compounds') in the presence of a catalyst, wherein the mixed gas including (meth)acrylic acid may include (meth) acrylic acid, non-reacted raw material compounds, (meth) acrolein, an inert gas, carbon monoxide, carbon dioxide, water vapor, and various organic byproducts (acetic acid, light ends, heavies, and the like), and the like. Herein, the term 'light ends' or 'heavies' commonly refers to a kind of byproduct that can be produced in the process of preparing and recovering aimed (meth)acrylic acid, and has a lower or higher molecular weight than (meth)acrylic acid.

Hereinafter, specific embodiments of the present invention will be explained in detail with reference to attached drawings so that a person having ordinary knowledge in the art can easily practice the present invention.

However, the present invention can be realized in many different forms, and is not limited to the embodiments explained herein.

The method of recovering (meth)acrylic acid includes the steps of: A) contacting a mixed gas including (meth)acrylic acid, organic byproducts, and water vapor with water in a (meth)acrylic acid absorption tower to form an aqueous solution of (meth)acrylic acid; B) discharging the (meth) acrylic acid aqueous solution of a first concentration, in a side part of the (meth)acrylic acid absorption tower; C) discharging the (meth)acrylic acid aqueous solution of a second concentration, in a lowest part of the (meth)acrylic acid absorption tower; B-1) contacting the (meth)acrylic acid aqueous solution of the first concentration discharged to the side part with an extraction solvent including a hydrophobic organic solvent in the (meth)acrylic acid extraction tower, to extract (meth)acrylic acid; and D) distilling the (meth)acrylic acid extract obtained in step B-1) and the (meth)acrylic acid aqueous solution of the second concentration discharged in step C), through an azeotropic distillation process, to obtain (meth)acrylic acid, wherein the first concentration has a lower (meth)acrylic acid concentration than the second concentration, and the method is progressed under conditions satisfying the following Mathematical Formula 1:

$$Y1 = a \times X1 \qquad \text{[Mathematical Formula 1]}$$

wherein, in Mathematical Formula 1,

Y1 is an amount of the extraction solvent used in step B-1), a is a ratio of the extraction solvent, and is equal to or greater than 2.5, and X1 is an amount of water included in the (meth)acrylic acid aqueous solution of the first concentration.

FIGS. 1 and 2 are process drawings of the recovery method of (meth)acrylic acid according to one embodiment of the present invention.

Referring to FIGS. 1 and 2, the method of recovering (meth)acrylic acid according to the present invention includes the steps of: A) contacting a mixed gas (1) including (meth)acrylic acid, organic byproducts, and water vapor with water in a (meth)acrylic acid absorption tower (100) to form an aqueous solution of (meth)acrylic acid; B) discharging the (meth)acrylic acid aqueous solution of the first concentration (103), at the side part of the (meth)acrylic acid absorption tower (100); C) discharging the (meth)acrylic acid aqueous solution of the second concentration (102), at the lowest part of the (meth)acrylic acid absorption tower (100); B-1) contacting the (meth)acrylic acid aqueous solution of the first concentration (103) discharged to the side part with an extraction solvent including a hydrophobic organic solvent in the (meth)acrylic acid extraction tower (200) to extract (meth)acrylic acid; and D) distilling the (meth)acrylic acid extract (203) obtained in step B-1) and the (meth)acrylic acid aqueous solution of the second concentration (102) discharged in step C), through an azeotropic distillation process, to obtain (meth)acrylic acid (303), wherein the first concentration has a lower (meth)acrylic acid concentration than the second concentration, and the process is progressed under conditions satisfying the above-explained Mathematical Formula 1.

According to the previously disclosed methods, an aqueous solution of (meth)acrylic acid is discharged at the lower part of a (meth)acrylic acid absorption tower (100) in a single stream, and is fed to a (meth)acrylic acid extraction tower (200), and using a hydrophobic solvent, a (meth)acrylic acid extract (203) is obtained, and the extract is distilled, thereby recovering (meth)acrylic acid.

However, the present inventors confirmed during studies on the existing (meth)acrylic acid recovery method that, if the concentration of discharged (meth)acrylic acid aqueous solution is to be increased so as to increase purification efficiency of (meth)acrylic acid, the separation efficiency of the (meth)acrylic acid absorption tower (100) is lowered, and if the concentration of discharged (meth)acrylic acid aqueous solution is maintained low so as to increase the separation efficiency, a purification (or distillation) load inevitably increases in the subsequent purification (or distillation) process.

Accordingly, as results of continuous studies, the present inventors confirmed that by discharging streams of different concentration values respectively at the side part and lower part of the (meth)acrylic acid absorption tower (100), and removing water in the low concentration stream discharged at the side part through a separate extraction process, and then introducing it into a distillation process together with the high concentration stream discharged at the lower part, a load may be decreased without lowering the separation efficiency in the subsequent distillation process, thus increasing energy efficiency, and completed the present invention.

First, the method of recovering (meth)acrylic acid according to one embodiment includes the step of contacting a mixed gas (1) including (meth)acrylic acid, organic byproducts, and water vapor, which are produced by a synthesis reaction of (meth)acrylic acid, with water in a (meth)acrylic acid absorption tower (100) to obtain an aqueous solution of (meth)acrylic acid. The absorption process means a process for obtaining the aqueous solution of (meth)acrylic acid in the (meth)acrylic acid absorption tower (100).

More specifically, the synthesis reaction of (meth)acrylic acid may be conducted by an oxidation reaction of one or more compounds selected from the group consisting of propane, propylene, butane, isobutylene, and (meth)acrolein in the presence of a gas phase catalyst.

Here, the gas phase oxidation reaction may be progressed in a gas phase oxidation reactor of a common structure and under common reaction conditions. As the catalyst in the gas phase oxidation reaction, a common catalyst may be used, and for example, the catalysts disclosed in Korean Registered Patent Nos. 0349602 and 037818 may be used.

In the mixed gas (1) including (meth)acrylic acid produced by the gas phase oxidation reaction, unreacted raw material compounds, intermediate (meth)acrolein, an inert gas, carbon dioxide, water vapor, and various organic byproducts (acetic acid, light ends, heavies, etc.) may be included, in addition to the target product (meth)acrylic acid.

Such a (meth)acrylic acid aqueous solution may be obtained in the form of an aqueous solution in which (meth)acrylic acid is dissolved, by feeding the mixed gas (1) including (meth)acrylic acid to a (meth)acrylic acid absorption tower (100) and contacting it with an absorption solvent water.

Here, the kind of the (meth)acrylic acid absorption tower (100) may be determined considering the contact efficiency of the mixed gas (1), the absorption solvent, etc., and for example, a packed column type of (meth)acrylic acid absorption tower or a multistage tray type of (meth)acrylic acid absorption tower may be used. The packed column type of (meth)acrylic acid absorption tower may include a packing material such as a Raschig ring, a pall ring, a saddle, a gauze, a structured packing type, etc. therein.

Further, considering the efficiency of the absorption process, the mixed gas (1) may be fed to the lower part of the (meth)acrylic acid absorption tower (100), and the absorption solvent including water may be fed to the upper part of the (meth)acrylic acid absorption tower (100).

The absorption solvent may include water such as tap water, deionized water, etc., and it may include recycled process water introduced from other processes (for example, process water recycled from an extraction process (201) and/or a distillation process (352). In addition, in the absorption solvent, a trace amount of organic byproducts (for example, acetic acid) introduced from other processes may be included. However, considering the absorption efficiency of (meth)acrylic acid, it is preferable to adjust such that the organic byproducts are included in an amount of 15 wt % or less in the absorption solvent fed to the (meth)acrylic acid absorption tower (100) (particularly, in the recycled process water).

Meanwhile, the (meth)acrylic acid absorption tower (100) may be operated under internal pressure of about 1 to about 1.5 bar, or about 1 to about 1.3 bar, and an internal temperature of about 50 to about 100° C., or about 50 to about 80° C., considering the moisture content according to (meth)acrylic acid condensation conditions and saturated vapor pressure.

Meanwhile, the (meth)acrylic acid aqueous solution obtained through the absorption process has a higher concentration toward the lower part in the (meth)acrylic acid absorption tower (100) because the absorption of (meth)acrylic acid is added, and in general, at the lowest part of the (meth)acrylic acid absorption tower (100), a concentration of about 70 to about 80% is formed.

According to one embodiment of the present invention, at the side part of the (meth)acrylic acid absorption tower (100), a (meth)acrylic acid aqueous solution of a first concentration (103) of a relatively low concentration is discharged, and at the lowest part, a (meth)acrylic acid aqueous solution of a second concentration (102) of a relatively high concentration is discharged.

Specifically, the first concentration may be about 40 wt % or less, preferably, about 30 wt % or less, or about 5 to about 30 wt %, and the second concentration may be about 60 wt % or more, preferably about 70 wt % or more, or about 70 to about 95 wt %.

However, the present invention is not necessarily limited to the above ranges, and the concentrations may be differently determined according to the process operation conditions such as temperature, pressure inside the (meth)acrylic acid absorption tower (100), etc., and the concentration of (meth)acrylic acid to be finally obtained.

Further, (meth)acrylic acid-stripped non-condensable gas (101) is discharged to the upper stage of the (meth)acrylic acid absorption tower (100).

Here, the side part of the (meth)acrylic acid absorption tower (100) means the side in the middle part of the (meth)acrylic acid absorption tower (100), i.e., the side at a point corresponding to about 40 to about 99, preferably about 30 to about 70 from the highest part to the lower position, when the highest part of the (meth)acrylic acid absorption tower is designated as 0 and the lowest part is designated as 100.

In the method of recovering (meth)acrylic acid of one embodiment, the (meth)acrylic acid aqueous solution (103) discharged at the side part and the (meth)acrylic acid aqueous solution (102) discharged at the lowest part are separately introduced in each process described below.

Meanwhile, according to one embodiment of the present invention, at least a part of the non-condensable gas (101) discharged to the upper part of the (meth)acrylic acid absorption tower may be fed to a process of recovering organic byproducts (particularly, acetic acid) included in the non-condensable gas (101) again, and the remainder may be fed to a waste gas incinerator and disposed of.

That is, according to one embodiment of the present invention, a process of contacting the non-condensable gas (101) with an absorption solvent to recover acetic acid included in the non-condensable gas (101) may be conducted.

The step of contacting the non-condensable gas (101) with an absorption solvent may be conducted in an acetic acid absorption tower (150). Here, for effective acetic acid absorption, the acetic acid absorption tower (150) may be adjusted to be operated under a pressure of about 1 to about 1.5 bar, preferably about 1 to about 1.3 bar, and a temperature of about 50 to about 100° C., preferably about 50 to about 80° C. Further, specific operation conditions of the acetic acid absorption tower (150) may be as described in Korean Laid-Open Patent Publication No. 2009-0041355.

Here, an acetic acid absorption solvent (151) for absorbing acetic acid may be fed to the upper part of the acetic acid absorption tower (150), and an aqueous solution containing acetic acid (152) may be discharged to the lower part of the acetic acid absorption tower (150). In addition, the acetic acid-containing aqueous solution (152) may be fed to the upper part of the (meth)acrylic acid absorption tower (100) and reused as an absorption solvent, and the acetic acid-stripped non-condensable gas (101) may be recycled to the synthesis reaction process of (meth)acrylic acid and reused.

As explained above, in case the (meth)acrylic acid aqueous solution of a relatively low concentration (103) is discharged directly from the side part of the (meth)acrylic acid absorption tower (100), since a relatively large amount of water (X1) is discharged together, the amount of water (X2) discharged to the lower part of the (meth)acrylic acid absorption tower (100) necessarily decreases, and thus, a (meth)acrylic acid aqueous solution of a high concentration (102) may be discharged to the lower part of the (meth) acrylic acid absorption tower (100).

In general, in a (meth)acrylic acid absorption tower discharging single stream, if the concentration of (meth)acrylic acid discharged to the lower part of the (meth)acrylic acid absorption tower is increased, the absorption efficiency of the (meth)acrylic acid absorption tower may decrease, and the content of (meth)acrylic acid may increase in the non-condensable gas discharged to the upper part of the (meth) acrylic acid absorption tower, and thus a loss of (meth) acrylic acid may be generated.

However, as described in the present invention, in case a (meth)acrylic acid aqueous solution of a relatively low concentration (103) is discharged directly from the side part of the (meth)acrylic acid absorption tower (100), the concentration of (meth)acrylic acid (102) discharged to the lowest part of the (meth)acrylic acid absorption tower (100) may be further increased without substantially influencing the absorption efficiency of the (meth)acrylic acid absorption tower (100), and the (meth)acrylic acid aqueous solution of a low concentration (103) that is discharged separately may also be recovered easily through a simple extraction process described below.

According to one embodiment of the present invention, it is preferable that the (meth)acrylic acid aqueous solution of the first concentration (103) discharged to the side part is discharged at a rate of about 10 wt % to about 50 wt %, based on the (meth)acrylic acid aqueous solution of the second concentration (102) discharged to the lowest part, and that the process is progressed under conditions satisfying the following Mathematical Formula 2.

$$0.01 \leq X1/(X1+X2) \leq 0.7 \qquad \text{[Mathematical Formula 2]}$$

In Mathematical Formula 2,

X1 is an amount of water in the (meth)acrylic acid aqueous solution of the first concentration (103), and X2 is an amount of water in the (meth)acrylic acid aqueous solution of the second concentration (102).

Here, X1+X2 corresponds to the total amount of water discharged during the absorption process used in the present invention, and it may correspond to the total amount of water discharged to the lower part in the existing process of discharging a single stream in the absorption tower.

When the process is progressed with the above-described discharge rate of the (meth)acrylic acid aqueous solution of the first concentration (103) and the (meth)acrylic acid aqueous solution of the second concentration (102) while maintaining relative amounts of discharged water within the above range, the amount of (meth)acrylic acid washed away through the non-condensable gas (101) discharged to the upper part may be minimized Preferably, the rate of X1 to the total amount of water discharged in the absorption process may be about 0.1 to about 0.7.

Further, in case the relative amounts of water discharged to the side part and the lower part satisfy the above ranges, a process load may decrease in the subsequent extraction or distillation process for obtaining (meth)acrylic acid from the (meth)acrylic acid aqueous solution with high purity.

Specifically, for example, if the amount of water (X1) included in the (meth)acrylic acid aqueous solution of the first concentration (103) becomes relatively greater, the amount of an extraction organic solvent required in the subsequent extraction process for extracting (meth)acrylic acid therefrom may increase, and in this case, the use of an azeotropic solvent additionally introduced in the distillation process may relatively decrease, thus decreasing the process load in the distillation process and increasing energy efficiency, while the purification efficiency may decrease in the distillation process, thus increasing loss of acrylic acid.

To the contrary, if the amount of water (X1) included in the (meth)acrylic acid aqueous solution of the first concentration (103) becomes relatively smaller, the amount of an extraction organic solvent for extracting (meth)acrylic acid therefrom may decrease, and in this case, the amount of an azeotropic solvent additionally introduced in the distillation process may increase, and thus acrylic acid purification efficiency may increase in the distillation process, and acrylic acid loss may decrease, while the amount of water removed in the extraction tower may decrease, and thus, the above-explained advantageous effect of the present invention, i.e., an energy efficiency increase, may be reduced.

Meanwhile, the method of recovering (meth)acrylic acid further includes the step of contacting the (meth)acrylic acid aqueous solution of the first concentration (103) discharged to the side part of the (meth)acrylic acid absorption tower (100) with an extraction solvent (302) including a hydrophobic organic solvent in the (meth)acrylic acid extraction tower (200), to extract (meth)acrylic acid.

In the (meth)acrylic acid extraction tower (200), the (meth)acrylic acid aqueous solution of the first concentration (103) contacts the extraction solvent (302), and may be discharged respectively as a (meth)acrylic acid extract (203) in which a significant amount of (meth)acrylic acid is dissolved, and a raffinate from which a significant amount of (meth)acrylic acid has been removed.

Further, in the (meth)acrylic acid extraction tower (200), relatively light (meth)acrylic acid extract (203) is obtained through the upper outlet, and relatively heavy raffinate is discharged through the lower outlet of the (meth)acrylic acid extraction tower (200).

Before the raffinate is discharged from the (meth)acrylic acid extraction tower (200), a certain amount thereof exists in a stationary state in the lower stationary section of the (meth)acrylic acid extraction tower (200), and a part thereof may be discharged to the lower outlet of the (meth)acrylic acid extraction tower (200) and a part thereof may be reused as a (meth)acrylic acid absorption solvent (201) for absorbing (meth)acrylic acid in the (meth)acrylic acid absorption tower (100).

As explained, by contacting the (meth)acrylic acid aqueous solution with an extraction solvent in the (meth)acrylic acid extraction tower (200), most of water included in the (meth)acrylic acid aqueous solution may be removed. Thus, the treatment load of the subsequent distillation process may be reduced, thereby improving energy efficiency of the total process.

Furthermore, by lowering the treatment load of the distillation process, the polymerization reaction of (meth)acrylic acid that can be generated during distillation may be minimized, and the recovery rate of (meth)acrylic acid may be further improved.

Meanwhile, the extraction solvent (302) fed to the (meth) acrylic acid extraction tower (200) includes a hydrophobic organic solvent, and it may further include organic byproducts, and for example, it may be a recycled process solvent introduced from other processes described below.

Specifically, the extraction solvent may include one or more hydrophobic solvents selected from the group consisting of benzene, toluene, xylene, n-heptane, cycloheptane, cycloheptene, 1-heptene, ethyl-benzene, methyl-cyclohexane, n-butyl acetate, isobutyl acetate, isobutyl acrylate, n-propyl acetate, isopropyl acetate, methyl isobutyl ketone, 2-methyl-1-heptene, 6-methyl-1-heptene, 4-methyl-1-heptene, 2-ethyl-1-hexene, ethylcyclopentane, 2-methyl-1-hexene, 2,3-dimethylpentane, 5-methyl-1-hexene, and isopropyl-butyl-ether, and preferably, it may be benzene, toluene, or xylene.

The (meth)acrylic acid extraction tower (200) is not specifically limited as long as it is a common extraction column according to a liquid-liquid contact method.

For example, it may be a Karr type reciprocating plate column, a rotary-disk contactor, a Scheibel column, a Kühni column, a spray extraction tower, a packed extraction tower, a pulsed packed column, etc.

Through the extraction process, a (meth)acrylic acid extract (203) is discharged to the upper part of the (meth) acrylic acid extraction tower (200), and it may be conveyed to an azeotropic distillation tower (300) through a transfer line.

Further, a raffinate is discharged to the lower part of the (meth)acrylic acid extraction tower (200), and a part of the discharged raffinate, which includes water, may be recycled as explained above and reused as a (meth)acrylic acid absorption solvent (201) in the (meth)acrylic acid absorption tower (100). In case the (meth)acrylic acid absorption solvent (201) is used as an absorption solvent of the absorption tower, it may be fed to the upper part of the (meth)acrylic acid absorption tower (100) through immediate phase separation at the lower part of the (meth)acrylic acid extraction tower (200), or it may be used in a distillation process described below, conveyed to a phase separation tank (350) together with the azeotropic solvent included in the upper discharge liquid (304) discharged to the upper part of the azeotropic distillation tower, phased-separated, and then fed as an absorption solvent (352) of the (meth)acrylic acid absorption tower (100).

Here, in the extract, besides a target compound (meth) acrylic acid, extraction solvents, water, and organic byproducts may be included. According to one embodiment, under a steady state in which stable operation is conducted, about 2 to about 20 wt % of (meth)acrylic acid, about 75 to about 98 wt % of extraction solvents, about 0.01 to about 2 wt % of water, and the remaining amount of organic byproducts may be included in the extract.

Through the extraction process, most of the water included in the (meth)acrylic acid aqueous solution may be recovered as a raffinate. As most of the water is recovered during the extraction process, an operation load of a distillation process described below may be reduced and energy consumption may be significantly decreased. In addition, since distillation conditions may be mitigated through it, for example, a polymerization reaction of (meth)acrylic acid may be minimized in a distillation process, thus securing operation stability and improving recovery efficiency of (meth)acrylic acid.

The step of extracting (meth)acrylic acid is progressed under conditions satisfying the following Mathematical Formula 1.

$$Y1 = a \times X1 \qquad \text{[Mathematical Formula 1]}$$

In Mathematical Formula 1,

Y1 is an amount of the extraction solvent used in step B-1), a is a ratio of the extraction solvent and is equal to or greater than 2.5, and X1 is an amount of water included in the (meth)acrylic acid aqueous solution of the first concentration (103).

The a is the ratio of the extraction solvent, i.e., the amount of the extraction amount used to the amount of water fed to the (meth)acrylic acid extraction tower (200), it may vary according to the extraction solvent practically used, and it may be about 2.5 or more, preferably about 2.7 or more, and about 4.0 or less, preferably about 3.5 or less, for extraction efficiency. However, the present invention is not necessarily limited to the above range, and as explained above, it may be differently set considering the kind of extraction solvents used in the extraction process, the efficiency of the extraction process and process load in a distillation process described below, etc.

That is, the weight ratio of the extraction solvent (Y1) to water (X1) in the (meth)acrylic acid aqueous solution of the first concentration (103) fed to the (meth)acrylic acid extraction tower (200) should be about 2.5 or more, preferably about 2.7 or more, and about 4.0 or less, preferably about 3.5 or less.

As such, by limiting the amount of the extraction solvent of the extraction process within a certain range, extraction efficiency may be maximized, and simultaneously, a subsequent azeotropic distillation process may be stably operated.

In the extraction process, if the weight ratio of the extraction solvent to water in the (meth)acrylic acid aqueous solution is less than 2.5, the concentration of (meth)acrylic acid in the raffinate may increase, which may deteriorate (meth)acrylic acid purification efficiency in the whole process.

In addition, as the weight ratio of the extraction solvent to water in the (meth)acrylic acid aqueous solution increases, the extraction efficiency in the (meth)acrylic acid extraction process (200) may be improved, however, since the amount of an azeotropic solvent separately fed to the upper part of an azeotropic distillation tower should be decreased in the subsequent azeotropic distillation process, distillation efficiency may be significantly lowered, thus increasing loss of (meth)acrylic acid.

Further, the raffinate obtained from the (meth)acrylic acid extraction tower (200) may consist mostly of water, and non-extracted (meth)acrylic acid and organic byproducts may be included therein.

Specifically, according to one embodiment of the invention, a very small amount of (meth)acrylic acid, such as in the concentration of about 10 wt % or less or about 0.1 to about 5 wt %, may be included in the raffinate, thus minimizing loss of (meth)acrylic acid in the absorption process and extraction process.

The method of recovering (meth)acrylic acid according to the embodiment of the present invention includes the step of conducting azeotropic distillation of the (meth)acrylic acid extract (203) and the (meth)acrylic acid aqueous solution of the second concentration (102) discharged in the step C) to obtain (meth)acrylic acid.

The solvent used in the azeotropic distillation is preferably a hydrophobic solvent that can form an azeotrope with water and acetic acid, and does not form an azeotrope with (meth)acrylic acid. The hydrophobic azeotropic solvent preferably has a boiling point lower than that of (meth)acrylic acid (for example, a boiling point of about 120° C. or less, about 10 to about 120° C., or about 50 to about 120° C.).

Specifically, the hydrophobic azeotropic solvent may be one or more solvents selected from the group consisting of benzene, toluene, xylene, n-heptane, cycloheptane, cycloheptene, 1-heptene, ethyl-benzene, methyl-cyclohexane, n-butyl acetate, isobutyl acetate, isobutyl acrylate, n-propyl acetate, isopropyl acetate, methyl isobutyl ketone, 2-methyl-1-heptene, 6-methyl-1-heptene, 4-methyl-1-heptene, 2-ethyl-1-hexene, ethylcyclopentane, 2-methyl-1-hexene, 2,3-dimethylpentane, 5-methyl-1-hexene and isopropyl-butyl-ether, and preferably, it may be benzene, toluene or xylene.

According to one embodiment of the invention, the (meth)acrylic acid extract (203) fed from the above-explained extraction process is fed to an azeotropic distillation tower (300) through a transfer line.

Here, in order to achieve effective distillation, the (meth)acrylic acid extract (203) is preferably fed to one stage corresponding to about 25 to about 75%, more preferably, one stage corresponding to about 25 to about 50% from the highest stage to the lower position, based on the total stages of the azeotropic distillation tower (300).

The (meth)acrylic acid extract (203) fed to the azeotropic distillation tower (300) includes (meth)acrylic acid and an extraction solvent (Y1) used in the previous extraction process, and considering the production efficiency according to the continuous process, it is preferable that the azeotropic solvent is identical to the extraction solvent of the extraction process.

That is, if the inside of the azeotropic distillation tower (300) is appropriately heated, by the extraction solvent (Y1) included in the (meth)acrylic acid extract (203) and the azeotropic solvent (Y2) introduced from the upper part of the azeotropic distillation tower (300), azeotropic distillation with water and acetic acid fed to the feed stage of the azeotropic distillation tower (300) may be achieved.

According to one embodiment of the invention, the azeotropic distillation process may be preferably progressed under conditions satisfying the following Mathematical Formula 3.

$$Y = b \times X2 \qquad \text{[Mathematical Formula 3]}$$

In Mathematical Formula 3,

Y is an amount of an azeotropic solvent used in step D), b is an azeotropic ratio, and X2 is an amount of water included in the (meth)acrylic acid aqueous solution of the second concentration.

Since most water is removed in the previous extraction process of (meth)acrylic acid extraction tower (200) and the amount of water included in the extract is very small, the amount of water fed to the distillation tower may be considered to be equal to the amount that was included in the (meth)acrylic acid aqueous solution (102) of the second concentration (X2).

The b is the azeotropic ratio referring to the amount of the azeotropic solvent used to the amount of water (X2) fed to the azeotropic distillation tower (300), it may vary according to the azeotropic solvent practically used, and may be preferably about 4 or more, or about 5 or more, and more preferably about 5.5 to about 8.5, but the present invention is not limited thereto, and it may be differently set considering the kind of the azeotropic solvent used in the distillation process, the efficiency and the process load of the azeotropic distillation process, the process load of the previous extraction process, etc.

Through the azeotropic distillation process, remaining ingredients other than (meth)acrylic acid in the (meth)acrylic acid extract (203) and the (meth)acrylic acid aqueous solution of the second concentration (102) discharged in the step C) are discharged to the upper part of the azeotropic distillation tower (300) together with the azeotropic solvent (304), and (meth)acrylic acid is discharged to the lower part (303).

Here, the upper discharge liquid (304) of the azeotropic distillation tower (300) is fed to a phase separation tank (350) and may be reused after a predetermined treatment. The phase separation tank (350) is an apparatus for separating liquid phases immiscible with each other by gravity, centrifugal force, etc., wherein a relatively light liquid (for example, an organic phase) may be recovered to the upper part of the phase separation tank, and a relatively heavy liquid (for example, an aqueous phase) may be recovered to the lower part of the phase separation tank.

For example, the upper discharge liquid (304) of the azeotropic distillation tower (300) and a part of the raffinate (201) discharged from the (meth)acrylic acid extraction tower (200) may be separated into an organic phase including solvent and an aqueous phase including water in the phase separation tank (350).

Here, a separated organic phase (351) may be fed to the upper stage of the azeotropic distillation tower (300) and used as an azeotropic solvent (301), and at least a part of the organic phase (351) may be fed to the (meth)acrylic acid extraction tower (200) and used as an extraction solvent (302).

Further, at least a part of the aqueous phase (352) separated in the phase separation tank may be fed to the (meth)acrylic acid absorption tower (100) and used as an absorption solvent (352) again, and a part thereof may be disposed as waste water. In the aqueous phase, acetic acid may be included, and the concentration of acetic acid included in the aqueous phase may vary according to the kind of the azeotropic solvent, the reflux ratio, etc.

According to one embodiment of the invention, the azeotropic distillation process may be preferably progressed under conditions satisfying the following Mathematical Formulas 4 and 5.

$$Y = Y1 + Y2 \qquad \text{[Mathematical Formula 4]}$$

$$Y2 > Y1 \qquad \text{[Mathematical Formula 5]}$$

In the Mathematical Formulas 4 and 5,

Y is the total amount of the azeotropic solvent used in step D),

Y1 is the amount of the extraction solvent used in step B-1), and

Y2 is the amount of the azeotropic solvent separately added from the upper part of the azeotropic distillation tower (300) in step D).

As explained above, considering the production efficiency according to a continuous process, it is preferable that the extraction solvent (Y1) and the azeotropic solvent (Y2) separately added in the azeotropic distillation process are identical to each other, and since the extraction solvent (Y1) and the azeotropic solvent (Y2) separately added in the azeotropic distillation process are separated as an organic phase through the treatment in the above-explained phase separation tank (350) and reused for extraction and azeotropic distillation, the amount of the hydrophobic organic solvent recycled in the whole process is identical to the total amount of the azeotropic solvent (Y) used in the azeotropic distillation step D), and is fixed to the sum of the extraction solvent (Y1) used in the extraction process of step B-1) and the azeotropic solvent (Y2) separately introduced in the azeotropic distillation process of step D).

Here, it is preferable that, in the organic phase (351, Y) separated through the treatment in the phase separation tank (350), the amount of the azeotropic solvent (301, Y2) separately introduced in the azeotropic distillation process is larger than the amount of the extraction solvent (302, Y1) that is recycled to the extraction process and flows in the azeotropic distillation tower (300) together with the (meth)acrylic acid extract (203).

If the amount of the azeotropic solvent (301, Y2) separately introduced in the upper part of the azeotropic distillation tower (300) is smaller than the amount of the extraction solvent (302, Y1) flowing in the azeotropic distillation tower (300) together with the (meth)acrylic acid extract (203), the amount of (meth)acrylic acid that is included in the upper discharge liquid (304) discharged to the upper part of the azeotropic distillation tower (300) and is lost may increase, thus significantly deteriorating the efficiency of azeotropic distillation.

While the (meth)acrylic acid aqueous solution passes through the (meth)acrylic acid absorption tower (100), the (meth)acrylic extraction tower (200), the azeotropic distillation tower (300), etc., at least a part of (meth)acrylic acid included in the aqueous solution may form dimers or oligomers. In order to minimize such polymerization of (meth)acrylic acid, a common polymerization inhibitor may be added to the azeotropic distillation tower (300).

In the lower discharge liquid (303) of the azeotropic distillation tower (300), heavies such as polymers of (meth)acrylic acid, a polymerization inhibitor, etc, may be included in addition to (meth)acrylic acid. Thus, if necessary, a step of feeding the lower discharge liquid of the azeotropic distillation tower (300) to a heavies separation tower (400) and separating heavies included in the lower discharge liquid (303) may be additionally conducted.

Further, crude (meth)acrylic acid (CAA) recovered through the above process may be passed through an additional crystallization process and obtained as high purity (meth)acrylic acid (HPAA). Here, since the separation process of heavies and the crystallization process may be conducted under common conditions, the process conditions are not specifically limited.

In such a recovery method of (meth)acrylic acid, the above-explained steps may be conducted organically and continuously. Further, in addition to the above-explained steps, commonly conducted processes may be further included and operated before, after, or simultaneously with each step.

Such a process may be progressed through an apparatus consisting of a (meth)acrylic acid absorption tower (100), a (meth)acrylic acid extraction tower (200), and an azeotropic distillation tower (300).

More specifically, the apparatus may include a (meth)acrylic acid absorption tower (100); a (meth)acrylic acid extraction tower (200) where a (meth)acrylic acid aqueous solution of a first concentration (103) discharged from the side part of the (meth)acrylic acid absorption tower (100) is made to contact an extraction solvent including a hydrophobic organic solvent, to extract (meth)acrylic acid; and a (meth)acrylic acid azeotropic distillation tower (300) where the (meth)acrylic acid extract (203) and a (meth)acrylic acid aqueous solution of a second concentration (102) discharged from the lowest part of the (meth)acrylic acid absorption tower (100) are distilled to obtain (meth)acrylic acid.

The (meth)acrylic acid absorption tower (100) may be a packed column type of (meth)acrylic acid absorption tower or a multistage tray type of (meth)acrylic acid absorption tower, and the packed column type of (meth)acrylic acid absorption tower may have a packing material such as a Raschig ring, a pall ring, a saddle, gauze, structured packing, etc., therein.

Particularly, in the (meth)acrylic acid absorption tower (100) of one embodiment, the first concentration outlet may be positioned at one point corresponding to about 40 to about 99%, and preferably one point corresponding to about 60 to about 80%, from the highest part of the (meth)acrylic acid absorption tower (100) to the lower position. If the first concentration outlet is equipped within the above range, absorption efficiency of the (meth)acrylic acid absorption tower (100) may be maximized, and a process load in the subsequent extraction process and azeotropic distillation process may be minimized.

In the apparatus of one embodiment, basically, the (meth)acrylic acid absorption tower (100) may be connected with the (meth)acrylic acid extraction tower (200) through a transfer line of the (meth)acrylic acid aqueous solution of the first concentration (103) of the side part. In addition, the (meth)acrylic acid extraction tower (200) may be connected with the azeotropic distillation tower (300) through a (meth)acrylic acid extract (203) transfer line, and the (meth)acrylic acid absorption tower (100) may be directly connected with the azeotropic distillation tower (300) through a transfer line of the (meth)acrylic acid aqueous solution of the second concentration (102) of the lowest part.

As the (meth)acrylic acid extraction tower (200), a common (meth)acrylic acid extraction tower (200) according to a liquid-liquid contact method may be used without specific limitations. As non-limiting examples, the (meth)acrylic acid extraction tower (200) may be a Karr type of reciprocating plate column, a rotary-disk contactor, a Scheibel column, a Kühni column, a spray extraction tower, a packed extraction tower, a pulsed packed column, etc.

The solvent recovery tower and the azeotropic distillation tower (300) may be equipped with a packed column or a multistage column including the above-explained packing material therein, and preferably a sieve tray column or a dual flow tray column.

Further, the recovery apparatus of (meth)acrylic acid according to the present invention may have a construction that is common in the technical field to which the present invention pertains.

Hereinafter, the actions and effects of the invention will be explained in more detail through specific examples of the invention. However, these examples are presented only as illustrations of the invention, and the scope of the right of the present invention is not limited thereby.

EXAMPLES (Meth)Acrylic Acid Absorption Process

Absorption Process Example 1

A (meth)acrylic acid absorption tower (100) equipped with an absorption section at the upper part and a cooling section at the lower part, and including a heat exchanger for cooling the lower condensate and reintroducing it to the (meth)acrylic acid absorption tower (100), was prepared.

The absorption section, with an inner diameter of 70.6 cm, consisted of 39 stages of sieve trays including a downcomer, at intervals of 7 cm.

The cooling section, with an inner diameter of 100 cm, positioned immediately below the absorption section, consisted of four stages of dual flow trays with an aperture ratio of 17% and a hole ID of 3 mm, at intervals of 10 cm.

The condensed liquid at the lower part of the (meth) acrylic acid absorption tower (100) was passed through an indirect heat exchanger and cooled, then reintroduced to the highest stage of the cooling section (the highest stage of the dual flow tray), thus constantly maintaining the temperature of the highest part of the (meth)acrylic acid absorption tower (100).

The mixed gas (1) including acrylic acid was prepared as a diluted gas at 165° C., by contacting 100 l/min $N_2$ heated to a high temperature of 800° C. with 46.2 g/min of an aqueous solution including 60.9 wt % of acrylic acid, 1.85 wt % of acetic acid, and 37.25 wt % of water, and it was introduced from the lower part of the (meth)acrylic acid absorption tower (100).

At the highest stage of the (meth)acrylic acid absorption tower (100), absorption water including 1.66 wt % of acrylic acid and 8.2 wt % of acetic acid was introduced at 18.23 g/min.

At the 27$^{th}$ sieve tray from the highest stage of the (meth)acrylic acid absorption tower (100), 8.79 g/min of the acrylic acid aqueous solution of the first concentration was discharged using a pump (hereinafter referred to as discharge stage number). In the acrylic acid aqueous solution of the first concentration, the concentrations of acrylic acid and acetic acid were 21.66 wt % and 3.84 wt %, respectively.

The acrylic acid aqueous solution of the second concentration was discharged through the lower part of the (meth) acrylic acid absorption tower (100) so that the temperature of the highest stage of the (meth)acrylic acid absorption tower (100) was constantly maintained at 64° C., and the level of the lower liquid of the (meth)acrylic acid absorption tower (100) was constantly maintained.

After the (meth)acrylic acid absorption tower (100) was operated for about 10 hours, the discharge flow rate of the lower liquid of the (meth)acrylic acid absorption tower (100), i.e., the flow rate of the acrylic acid aqueous solution of the second concentration, was 33.49 g/min, and the concentrations of acrylic acid and acetic acid were 77.65 wt % and 2.38 wt %, respectively.

The non-condensable gas (101) discharged to the upper part of the (meth)acrylic acid absorption tower (100) was discharged at 147.22 g/min, the concentration of acrylic acid in the discharge gas was 0.41 wt % and the ratio of $H_2O/N_2$ was 16.4:100, the temperature of the discharged acrylic acid aqueous solution of the second concentration was 76.3° C., and the pressures of the highest stage and the lowest stage of the (meth)acrylic acid absorption tower (100) were 117 mbar and 162 mbar, respectively.

The ratio of the amount of water included in the acrylic acid aqueous solution of the first concentration and the amount of water included in the acrylic acid aqueous solution of the second concentration was 5:5 (hereinafter, water ratio).

Absorption Process Examples 2 to 9

The absorption processes of (meth)acrylic acid were progressed by the same method as Example 1, except that the stage numbers where the acrylic acid aqueous solution of the first concentration were discharged and the flow rates were varied.

Absorption Process Comparative Example 1

A single acrylic acid stream of the second concentration was discharged to the lower part, without side discharge.

A (meth)acrylic acid absorption tower (100) equipped with an absorption section at the upper part and a cooling section at the lower part, and including a heat exchanger for cooling the lower condensate and reintroducing it to the (meth)acrylic acid absorption tower (100), was prepared.

The absorption section, with an inner diameter of 70.6 cm, consisted of 39 stages of sieve trays including a downcomer at intervals of 7 cm.

The cooling section, with an inner diameter of 100 cm, positioned immediately below the absorption section, consisted of 4 stages of dual flow trays with an aperture ratio of 17% and a hole ID of 3 mm, at intervals of 10 cm.

The condensed liquid at the lower part of the (meth) acrylic acid absorption tower (100) was passed through an indirect heat exchanger and cooled, then reintroduced to the highest stage of the cooling section (the highest stage of the dual flow tray), thus constantly maintaining the temperature of the highest part of the (meth)acrylic acid absorption tower (100).

The mixed gas (1) including acrylic acid was prepared as a diluted gas at 165° C. by contacting 100 l/min $N_2$ heated to a high temperature of 800° C. with 46.2 g/min of an aqueous solution including 60.9 wt % of acrylic acid, 1.85 wt % of acetic acid, and 37.25 wt % of water, and it was introduced from the lower part of the (meth)acrylic acid absorption tower (100).

At the highest stage of the (meth)acrylic acid absorption tower (100), absorption water including 1.73 wt % of acrylic acid and 8.13 wt % of acetic acid was introduced at 18.26 g/min.

The acrylic acid aqueous solution of the second concentration was discharged through the lower part of the (meth) acrylic acid absorption tower (100) so that the temperature of the highest stage of the (meth)acrylic acid absorption tower (100) was constantly maintained at 64° C., and the level of the lower liquid of the (meth)acrylic acid absorption tower (100) was constantly maintained.

After the (meth)acrylic acid absorption tower (100) was operated for about 10 hours, the discharge flow rate of the lower liquid of the (meth)acrylic acid absorption tower (100), i.e., the flow rate of the acrylic acid aqueous solution of the second concentration, was 42.05 g/min, and the concentrations of acrylic acid and acetic acid were 66.68 wt % and 2.68 wt %, respectively.

The non-condensable gas (101) discharged to the upper part of the (meth)acrylic acid absorption tower (100) was discharged at 147.41 g/min, the concentration of acrylic acid in the discharge gas was 0.40 wt % and the ratio of $H_2O/N_2$ was 16.4:100, the temperature of the discharged acrylic acid aqueous solution of the second concentration was 74.1° C., and the pressures of the highest stage and the lowest stage of the (meth)acrylic acid absorption tower (100) were 112 mbar and 160 mbar, respectively.

The process conditions of the absorption processes in the examples and comparative examples are summarized in the following Table 1, the indicators relating to the acrylic acid aqueous solution of the first concentration (103) discharged to the side part of the (meth)acrylic acid absorption tower (100) are summarized in Table 2, the indicators relating to the acrylic acid aqueous solution of the second concentration (102) discharged to the lower part of the (meth)acrylic acid absorption tower (100) are summarized in Table 3, and the indicators relating to the non-condensable gas (101) discharged to the upper part of the (meth)acrylic acid absorption tower (100) are summarized in Table 4.

TABLE 1

| | Discharge stage number (stage) | Temperature*- (102) (° C.) | Pressure (highest stage/ lowest stage) (mbar) | Water ratio |
|---|---|---|---|---|
| Example 1 | 27 | 76.3 | 117/162 | 5:5 |
| Example 2 | 8 | 76.1 | 114/160 | 5:5 |
| Example 3 | 16 | 76.2 | 116/163 | 5:5 |
| Example 4 | 23 | 76.7 | 116/164 | 5:5 |
| Example 5 | 35 | 75.1 | 113/161 | 5:5 |
| Example 6 | 27 | 75.3 | 117/165 | 31:69 |
| Example 7 | 27 | 75.6 | 115/165 | 40:60 |
| Example 8 | 27 | 77.2 | 115/163 | 60:40 |
| Example 9 | 27 | 78 | 118/165 | 70:30 |
| Comparative Example 1 | — | 74.1 | 112/160 | — |

Temperature*: temperature of the acrylic acid aqueous solution of the second concentration discharged to the lower part

TABLE 2

| (103) | Flow rate (g/min) | Concentration of acrylic acid (wt %) | Concentration of acetic acid (wt %) |
|---|---|---|---|
| Example 1 | 8.79 | 21.66 | 3.84 |
| Example 2 | 7.6 | 9.63 | 5.07 |
| Example 3 | 7.9 | 13.09 | 4.38 |
| Example 4 | 8.4 | 17.75 | 4.01 |
| Example 5 | 13.0 | 47.62 | 3.18 |
| Example 6 | 5.26 | 19.15 | 3.92 |
| Example 7 | 6.89 | 20.07 | 3.84 |
| Example 8 | 10.74 | 23.25 | 3.82 |
| Example 9 | 12.59 | 26.42 | 3.87 |
| Comparative Example 1 | — | — | — |

TABLE 3

| (102) | Flow rate (g/min) | Concentration of acrylic acid (wt %) | Concentration of acetic acid (wt %) |
|---|---|---|---|
| Example 1 | 33.49 | 77.65 | 2.38 |
| Example 2 | 34.55 | 77.45 | 2.31 |
| Example 3 | 34.05 | 78.10 | 2.33 |
| Example 4 | 33.37 | 79.13 | 2.35 |
| Example 5 | 28.98 | 74.10 | 2.42 |
| Example 6 | 36.98 | 72.37 | 2.49 |
| Example 7 | 35.30 | 75.15 | 2.44 |
| Example 8 | 31.58 | 80.62 | 2.31 |
| Example 9 | 29.52 | 83.30 | 2.19 |

TABLE 4

| (101) | Flow rate (g/min) | Concentration of acrylic acid (wt %) | $H_2O/N_2$ ratio (%) |
|---|---|---|---|
| Example 1 | 147.22 | 0.41 | 16.4 |
| Example 2 | 147.29 | 0.61 | 16.4 |
| Example 3 | 147.42 | 0.49 | 16.3 |
| Example 4 | 147.60 | 0.43 | 16.6 |
| Example 5 | 147.28 | 0.41 | 16.6 |
| Example 6 | 147.30 | 0.39 | 16.4 |
| Example 7 | 147.23 | 0.40 | 16.4 |
| Example 8 | 147.15 | 0.40 | 16.4 |
| Example 9 | 147.29 | 0.41 | 16.5 |
| Comparative Example 1 | 147.41 | 0.40 | 16.4 |

Referring to Tables 1 to 4, it can be confirmed that if a stream with a relatively low concentration of acrylic acid is separately discharged through the side part of the (meth) acrylic acid absorption tower (100) as in one embodiment of the present invention, the concentration of acrylic acid discharged to the lower part may be increased by about 10% or more without deterioration of separation efficiency, and simultaneously, the amount of acrylic acid that is included in the non-condensable gas discharged to the upper part of the absorption tower and is lost may be decreased. It can also be confirmed that as the acrylic acid aqueous solution of the first concentration is discharged at the stage positioned at the relatively lower part, absorption efficiency increases.

However, as the acrylic acid aqueous solution of the first concentration is discharged at the lower part, the concentration of acrylic acid in the acrylic acid aqueous solution of the first concentration increases, and in this case, the process load may increase in the subsequent (meth)acrylic acid extraction process or azeotropic distillation process, and in this regard, it can be confirmed that, when the (meth)acrylic acid aqueous solution of the first concentration is discharged at a stage corresponding to the height of about 40 to about 99%, more preferably at a stage corresponding to the height of about 60 to about 80%, from the highest part of the (meth)acrylic acid absorption tower to the lower position, the efficiency of the whole process may be significantly increased.

Extraction Process of (Meth)Acrylic Acid

Extraction Process Comparative Example 1

A (meth)acrylic acid extraction tower (200), with an inner diameter of 22 mm, consisted of a total of 56 stages of a Karr type of reciprocating plate column The acrylic acid aqueous solution of the first concentration (acrylic acid:21.06 wt %, acetic acid:4.15 wt %) was introduced into the first stage (the highest stage) of the (meth)acrylic acid extraction tower at 35.9 g/min.

As the extraction solvent, a part of the reflux stream including toluene, obtained as the organic phase (351) in the upper discharge liquid of the azeotropic distillation tower (300) was used, and the extraction solvent included 0.28 wt % of acrylic acid, 0.5 wt % of acetic acid, and the remaining amount of toluene.

The extraction solvent was introduced through the 56$^{th}$ stage (the lowest stage) of the (meth)acrylic acid extraction tower (200) at 59.48 g/min Under a steady state, the extract was discharged to the upper part of the (meth)acrylic acid extraction tower (200) at a flow rate of 66.67 g/min, and the extract included 10.1 wt % of acrylic acid, 0.75 wt % of acetic acid, 0.66 wt % of water, and the remaining amount of toluene.

A raffinate including 3.49 wt % of acrylic acid, 4.36 wt % of acetic acid, and the remaining amount of water was discharged to the lower part of the (meth)acrylic acid extraction tower (200).

During the operation of the (meth)acrylic acid extraction tower (200), the water removal rate for the acrylic acid aqueous solution of the first concentration was 98.4%, and the acrylic acid extraction rate was 87.0%.

During the operation of the (meth)acrylic acid extraction tower (200), the ratio (a) of the extraction solvent introduced into the (meth)acrylic acid extraction tower (200)/water was 2.18.

The operation conditions and the products are summarized in the following Table 5.

Extraction Process Examples 1 to 5

The operation of the (meth)acrylic acid extraction tower (200) was progressed by the same method as Comparative Example 1, except that the ratio (a) of the extraction solvent introduced into the (meth)acrylic acid extraction tower (200)/water was varied.

The operation conditions and the products are summarized in the following Table 5.

TABLE 5

| | | Acrylic acid extract | | | Raffinate | | | Acrylic |
|---|---|---|---|---|---|---|---|---|
| | Extraction solvent/water (weight ratio) | Acrylic acid concentration (wt %) | Acetic acid concentration (wt %) | Water concentration (wt %) | Acrylic acid concentration (wt %) | Acetic acid concentration (wt %) | Water removal rate (%) | acid extraction rate (%) |
| Example 1 | 2.7 | 8.86 | 0.74 | 0.39 | 2.34 | 4.39 | 98.8 | 91.3 |
| Example 2 | 3.3 | 7.42 | 0.64 | 0.62 | 2.03 | 4.61 | 97.8 | 92.7 |
| Example 3 | 2.92 | 9.72 | 0.82 | 0.26 | 2.52 | 5.18 | 99.2 | 92.1 |
| Example 4 | 3.44 | 8.41 | 0.73 | 0.44 | 1.89 | 5.53 | 98.3 | 94.1 |
| Example 5 | 4.01 | 7.50 | 5.76 | 0.21 | 1.52 | 5.76 | 99.1 | 95.2 |

Referring to Table 5, it can be clearly confirmed that, when the process is progressed at the weight ratio of an extraction solvent/water of about 2.5 or more, the water removal rate and acrylic acid extraction rate are significantly improved, and specifically, it can be clearly confirmed that the concentration of acrylic acid can be largely reduced in the raffinate. However, if the ratio of an extraction solvent/water is excessively increased, the amount of the extraction solvent (Y1) introduced in the extraction process may become relatively large, and thus, in the subsequent azeotropic distillation process, the introduction amount of refluxed azeotropic solvent (Y2) may decrease. Thus, considering the efficiency of the extraction process and the purification efficiency of the azeotropic distillation process, it is preferable that the ratio of the extraction solvent/water is maintained at about 2.5 to about 4.0.

Azeotropic Distillation Process

Azeotropic Distillation Process Example 1

As an azeotropic distillation tower (300), a column with the inner diameter of 300 mm were used (a total of 39 stages of sieve trays which include downcomers), and the operation pressure was maintained at 110 torr.

Based on the result of the extraction process Example 2, i.e., the extraction result obtained when the ratio of the extraction solvent introduced in the (meth)acrylic acid extraction tower (200)/water (a) was set up as 3.30, the (meth)acrylic acid extract (203) discharged to the upper part of the (meth)acrylic acid extraction tower (200) and the (meth)acrylic acid aqueous solution of the second concentration discharged to the lower part of the (meth)acrylic acid absorption tower (100) were introduced at the $20^{th}$ stage from the upper part of the azeotropic distillation tower (300), at flow rates of 20.9 g/min and 30.4 g/min, respectively.

As the azeotropic solvent (Y2), a part of the reflux stream including toluene, obtained as the organic phase (351) in the upper discharge liquid of the azeotropic distillation tower (300), was introduced at the first stage (the highest stage) of the azeotropic distillation tower (300), at 19.9 g/min (toluene).

Heat was supplied through a reboiler of the lower stage of the azeotropic distillation tower (300), so that the temperature of the $20^{th}$ stage from the upper part was maintained at about 68.9° C., and the temperature of the $15^{th}$ stage was maintained at about 46° C.

After stable operation was conducted for about 6 hours, under a steady state, 46.08 g/min of the upper discharge liquid (304) was discharged to the upper part of the azeotropic distillation tower (300), and in the lower part, the lower discharge liquid (303) including acrylic acid was obtained at a flow rate of 25.12 g/min.

Under a steady state, the temperature of the upper part of the azeotropic distillation tower (300) was maintained at about 40.2° C., and the temperature of the lower part was maintained at about 94.4° C.

The operation conditions and results of the azeotropic distillation tower are summarized in the following Table 6.

Azeotropic Distillation Process Comparative Example 1

As an azeotropic distillation tower (300), a column with the inner diameter of 300 mm were used (a total of 39 stages of sieve trays which include downcomer), and the operation pressure was maintained at 110 torr.

Based on the result of the absorption process Comparative Example 1, i.e., the result of discharging a single stream to the upper part, the (meth)acrylic acid aqueous solution of the second concentration discharged to the lower part of the (meth)acrylic acid absorption tower (100) was introduced at the $20^{th}$ stage from the upper part of the azeotropic distillation tower (300), at a flow rate of 20.4 g/min.

As the azeotropic solvent (Y2), a part of the reflux stream including toluene, obtained as the organic phase (351) in the upper discharge liquid of the azeotropic distillation tower (300), was introduced at the first stage (the highest stage) of the azeotropic distillation tower (300), at 39.66 g/min (toluene).

Heat was supplied through a reboiler of the lower stage of the azeotropic distillation tower (300), so that the temperature of the $20^{th}$ stage from the upper part was maintained at about 69° C., and the temperature of the $15^{th}$ stage was maintained at about 45° C.

After stable operation was conducted for about 6 hours, under a steady state, 46.78 g/min of the upper discharge liquid (304) was discharged to the upper part of the azeotropic distillation tower (300), and at the lower part, the lower discharge liquid (303) including acrylic acid was obtained at the flow rate of 13.28 g/min Under a steady state, the temperature of the upper part of the azeotropic distillation tower (300) was maintained at about 39.6° C., and the temperature of the lower part was maintained at about 94° C.

The operation conditions and results of the azeotropic distillation tower are summarized in the following Table 6.

TABLE 6

|  |  |  | 102 | 203 | 301 | 304 | 303 |
|---|---|---|---|---|---|---|---|
| Example 1 | Mass Flow (g/min) |  | 30.39 | 20.88 | 19.93 | 46.08 | 25.12 |
|  | Composition (wt %) | Toluene | 0 | 91.68 | 99.20 | 84.45 | 0 |
|  |  | Acrylic acid | 77.17 | 7.73 | 0.23 | 0.36 | 99.24 |
|  |  | Acetic acid | 2.38 | 0.59 | 0.57 | 2.03 | 0.044 |
|  |  | Water | 19.64 | 0 | 0 | 13.16 | 0 |
|  |  | Others | 0.81 | 0 | 0 | 0 | 0.716 |
| Comparative Example 1 | Mass Flow (g/min) |  | 20.4 | 0 | 39.66 | 46.78 | 13.28 |
|  | Composition (wt %) | Toluene | 0 | 0 | 99.6 | 84.45 | 0 |
|  |  | Acrylic acid | 64.52 | 0 | 0.08 | 0.14 | 98.83 |
|  |  | Acetic acid | 2.92 | 0 | 0.32 | 1.53 | 0.011 |
|  |  | Water | 31.7 | 0 | 0 | 13.88 | 0 |
|  |  | Others | 0.86 | 0 | 0 | 0 | 1.159 |

102: (meth)acrylic acid aqueous solution of second concentration, discharged from the lowest part of the acrylic acid absorption tower (100)
203: acrylic acid (meth)acrylic acid extract (203)
301: azeotropic solvent fed to the upper stage of the azeotropic distillation tower (300)
304: upper discharge liquid, discharged to the upper part of the azeotropic distillation tower
303: lower discharge liquid of the azeotropic distillation tower, including acrylic acid Referring to Table 6, it can be confirmed that, when acrylic acid included in the stream of low concentration is extracted in the (meth)acrylic acid extraction tower (200), by maintaining the ratio of water to the extraction solvent beyond a certain level, the acrylic acid concentration in the raffinate discharged to the lower part may be decreased by about 30% or more. Further, in the azeotropic distillation tower of the existing process, water was removed by azeotropic distillation together with the solvent, however, in the examples of the present invention, since water was removed as a raffinate discharged from the extraction tower without separate energy consumption, water removed in the azeotropic distillation decreased, thus decreasing the process load of the azeotropic distillation tower, and significantly decreasing total energy consumption.

EXPLANATION OF SYMBOLS

1: mixed gas
100: (meth)acrylic acid absorption tower
101: (meth)acrylic acid-stripped, non-condensable gas
102: (meth)acrylic acid aqueous solution of second concentration
103: (meth)acrylic acid aqueous solution of first concentration
150: acetic acid absorption tower
151: acetic acid absorption solvent
152: acetic acid containing aqueous solution
200: (meth)acrylic acid extraction tower
201: (meth)acrylic acid absorption solvent
203: (meth)acrylic acid extract
300: azeotropic distillation tower
301: azeotropic solvent separately introduced into the upper part of the azeotropic distillation tower
302: extraction solvent
303: lower discharge liquid of the azeotropic distillation tower
304: upper discharge liquid of the azeotropic distillation tower
350: phase separation tank
351: organic phase separated in the phase separation tank
352: aqueous phase separated in the phase separation tank, (meth)acrylic acid absorption solvent
400: heavies separation tower

The invention claimed is:

1. A method of recovering (meth)acrylic acid comprising the steps of:
   A) contacting a mixed gas comprising (meth)acrylic acid, organic byproducts, and water vapor with water in a (meth)acrylic acid absorption tower to form an aqueous solution of (meth)acrylic acid;
   B) discharging the (meth)acrylic acid aqueous solution of a first concentration, to the side part of the (meth)acrylic acid absorption tower;
   C) discharging the (meth)acrylic acid aqueous solution of a second concentration, to the lowest part of the (meth)acrylic acid absorption tower;
   B-1) contacting the (meth)acrylic acid aqueous solution of the first concentration discharged to the side part with an extraction solvent comprising a hydrophobic organic solvent in the (meth)acrylic acid extraction tower, to extract (meth)acrylic acid; and
   D) distilling the (meth)acrylic acid extract obtained in step B-1) and the (meth)acrylic acid aqueous solution of the second concentration discharged in step C), through an azeotropic distillation process, to obtain (meth)acrylic acid,
   wherein the first concentration has a lower (meth)acrylic acid concentration than the second concentration, and the following Mathematical Formula 1 is satisfied:

$$Y1 = a \times X1 \qquad \text{[Mathematical Formula 1]}$$

wherein, in Mathematical Formula 1,
   $Y1$ is an amount of the extraction solvent used in step B-1),
   $a$ is a ratio of the extraction solvent, and is equal to or greater than 2.5, and
   $X1$ is an amount of water included in the (meth)acrylic acid aqueous solution of the first concentration.

2. The method of recovering (meth)acrylic acid according to claim 1, wherein the (meth)acrylic acid aqueous solution of the first concentration is discharged at a point corresponding to the height of 40 to 99% from the highest part of the (meth)acrylic acid absorption tower to the lower position.

3. The method of recovering (meth)acrylic acid according to claim 1, wherein the step of forming the (meth)acrylic acid aqueous solution is progressed under pressure of 1 to 1.5 bar and a temperature of 50 to 100° C.

4. The method of recovering (meth)acrylic acid according to claim 1, wherein the (meth)acrylic acid aqueous solution of the first concentration comprises 40 wt % or less of (meth)acrylic acid.

5. The method of recovering (meth)acrylic acid according to claim 1, wherein the (meth)acrylic acid aqueous solution of the second concentration comprises 60 wt % or more of (meth)acrylic acid.

6. The method of recovering (meth)acrylic acid according to claim 1, wherein the (meth)acrylic acid aqueous solution of the first concentration discharged to the side part is discharged at a rate of 10 wt % to 50 wt %, based on the (meth)acrylic acid aqueous solution of the second concentration discharged to the lowest part.

7. The method of recovering (meth)acrylic acid according to claim 1, wherein the following Mathematical Formula 2 is satisfied:

$$0.01 \leq X1/(X1+X2) \leq 0.7 \quad \text{[Mathematical Formula 2]}$$

wherein, in Mathematical Formula 2,
X1 is an amount of water in the (meth)acrylic acid aqueous solution of the first concentration, and
X2 is an amount of water in the (meth)acrylic acid aqueous solution of the second concentration.

8. The method of recovering (meth)acrylic acid according to claim 1, wherein the following Mathematical Formula 3 is satisfied:

$$Y = b \times X2 \quad \text{[Mathematical Formula 3]}$$

wherein, in Mathematical Formula 3,
Y is an amount of an azeotropic solvent used in step D),
b is an azeotropic ratio, and
X2 is an amount of water included in the (meth)acrylic acid aqueous solution of the second concentration.

9. The method of recovering (meth)acrylic acid according to claim 1, wherein the extraction solvent used in step B-1) and the azeotropic solvent used in step D) are identical to each other, and the following Mathematical Formulas 4 and 5 are satisfied:

$$Y = Y1 + Y2 \quad \text{[Mathematical Formula 4]}$$

$$Y2 > Y1 \quad \text{[Mathematical Formula 5]}$$

wherein, in Mathematical Formulas 4 and 5,
Y is the total amount of the azeotropic solvent used in step D),
Y1 is the amount of the extraction solvent used in step B-1), and
Y2 is the amount of the azeotropic solvent added in step D).

* * * * *